United States Patent [19]

Mulhauser et al.

[11] Patent Number: 4,558,810
[45] Date of Patent: Dec. 17, 1985

[54] SURGICAL STAPLER CONSTRUCTION

[75] Inventors: Paul J. Mulhauser; Douglas M. Spranger; Malcolm J. Brookes; Karl D. Kirk, III, all of New York, N.Y.

[73] Assignee: Richard-Allan Medical Industries, Inc., Richland, Mich.

[21] Appl. No.: 560,074

[22] Filed: Dec. 9, 1983

[51] Int. Cl.$^4$ .............................................. A61B 17/04
[52] U.S. Cl. .................... 227/19; 128/334 R; 227/88; 227/DIG. 1
[58] Field of Search ................ 128/334 R, 334 C; 227/19, 83, 87, 88, DIG. 1

[56] References Cited

U.S. PATENT DOCUMENTS

| 456,415 | 7/1891 | Howenstine . | |
|---|---|---|---|
| 520,734 | 5/1894 | Greenfield . | |
| 1,434,936 | 11/1922 | Watson . | |
| 1,610,632 | 12/1926 | Svenson . | |
| 1,945,377 | 1/1934 | Posnack | 227/DIG. 1 |
| 3,917,145 | 11/1975 | Graf et al. | 227/90 |
| 4,109,844 | 8/1978 | Becht | 227/120 |
| 4,179,057 | 12/1979 | Becht et al. | 227/120 |
| 4,364,507 | 12/1982 | Savino | 227/DIG. 1 |
| 4,406,392 | 9/1983 | Campbell et al. | 227/19 |
| 4,411,378 | 10/1983 | Warman | 227/DIG. 1 |
| 4,523,695 | 6/1985 | Braun et al. | 227/19 X |
| 4,527,725 | 7/1985 | Foslien | 227/19 |

FOREIGN PATENT DOCUMENTS

| 69557 | 1/1983 | European Pat. Off. | 227/DIG. 1 |
|---|---|---|---|
| 815658 | 9/1956 | United Kingdom | 227/DIG. 1 |
| 189982 | 12/1966 | U.S.S.R. | 227/DIG. 1 |

*Primary Examiner*—Paul A. Bell
*Attorney, Agent, or Firm*—Neuman, Williams, Anderson & Olson

[57] ABSTRACT

A surgical stapler for implanting and clinching staples in the body of a patient employs a reciprocally movable, retractable anvil and a reciprocally movable former for forming a staple about the end of the retractable anvil. A toggle is mounted in a stapler trigger which simultaneously actuates the former and toggle. The toggle removes the anvil end into and out of the path of the former whereby desired release of a formed staple from the anvil is assured following clinching of the staple ends.

9 Claims, 10 Drawing Figures

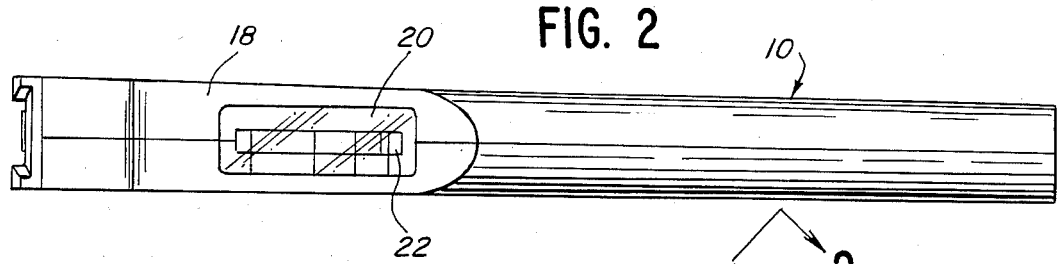
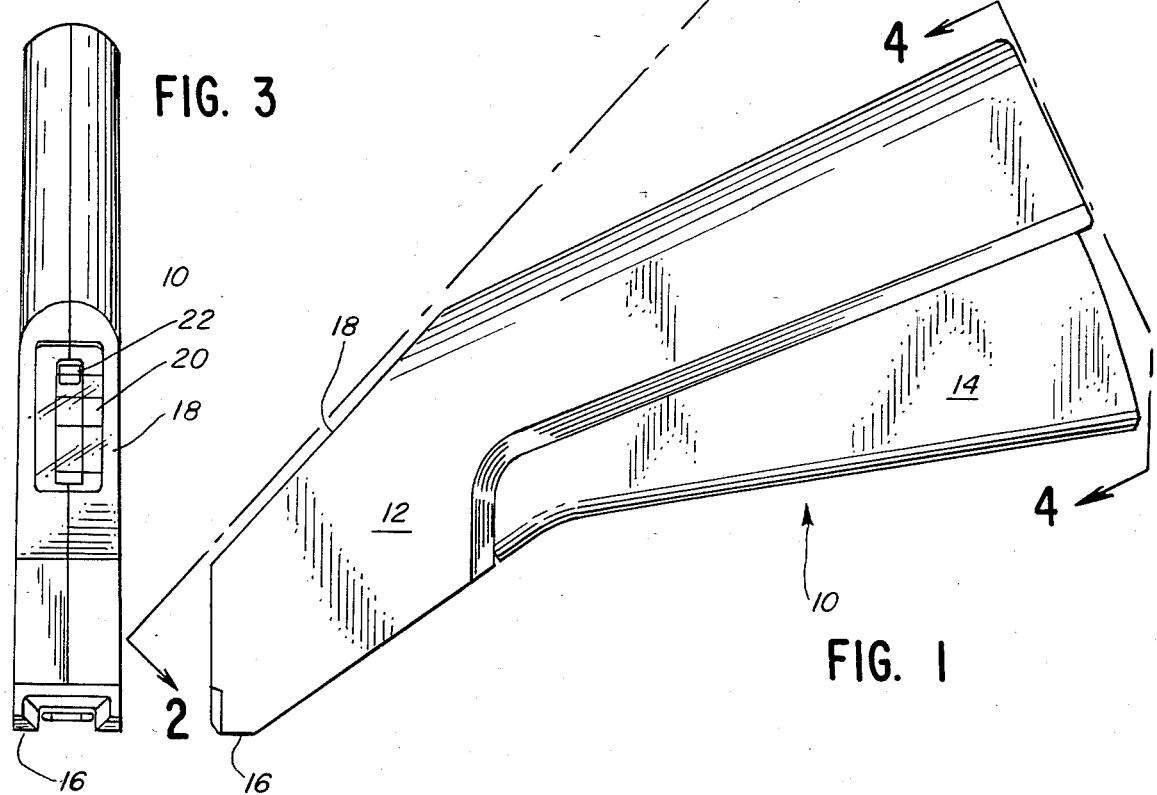
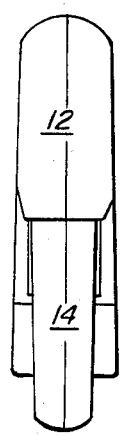

SURGICAL STAPLER CONSTRUCTION

This invention relates to a surgical stapler, and more particularly pertains to a surgical stapler of novel design which may be readily employed by medical personnel in a facile manner.

Surgical staplers are well-known in the art having been used for many years for purposes of rapidly closing openings which are formed by injury or by incision in the course of surgical procedures, in the bodies of patients. Surgical staplers possess the obvious advantage of speed as they are adapted to readily close such body openings. Speed of closure may be of critical importance as when vital fluids are being lost from the body of a patient. Such loss may be stopped or substantially lessened by rapid staple application. In such emergencies, tedious and time-consuming suturing is eliminated.

Although subtantially all surgical staplers are able to be employed for rapid staple application, they are subject to a variety of operational difficulties. The latter include jamming of staples within the stapler, and possible tearing of the patient's skin if the stapler is not withdrawn from the body in a particular direction after clinching of the staple.

Such difficulty exists when the staple remains engaged with a staple-forming anvil following staple clinching unless the stapler is withdrawn in a specific direction from the clinched staple to permit staple release from the anvil. Thus, when an emergency arises necessitating immediate closing of a body opening, attending medical personnel, unless having prior familiarity with the stapler, may attempt to remove the stapler from the staple clinched in the patient so as to tear the patient's skin. Also, even though having previous familiarity with such a stapler, the pressures of effecting immediate closure may cause the person employing the stapler to temporarily forget proper stapler operation resulting in the inadvertent tearing and possible attendant infliction of pain.

In accordance with this invention a substantially jam-proof stapler construction is provided in which the stapler may be readily removed from the staple clinched in the body of a patient. Such stapler removal or withdrawal may be effected in any direction whatsoever without danger of skin tearing or possible discomfort to the patient. Such withdrawal ability is made possible by the utilization of a novel staple-forming anvil which is automatically reciprocally moved into and out of the path of a staple former blade during stapler actuation by a novel toggle construction.

The prior art discloses a variety of stapler constructions which although incorporating a particular structural feature of the surgical stapler of this invention, does not render obvious the structure hereinafter defined in the appended claims. The prior art does not suggest the novel manner of surgical stapler operation inherent in the use of the construction hereinafter described in detail.

Thus, Greenfield U.S. Pat. No. 520,734 is directed to a book stapling device for stapling a plurality of cloth or paper sheets together, and in which staples are formed from a wire reel and driven into clinching engagement with the underlying sheet material. Although this device discloses a staple-forming mandrel which is cammed to the side of the path traversed by the staple-forming wire, it employs in addition a fixed anvil. Greenfield does not suggest the axial, rearward retraction of a staple anvil from the point of staple application. The Greenfield device was obviously not intended to bring the edges of a body incision together, and its structural features are such that it could not be positioned for such function.

Prior art staplers incorporating retractable staple-forming elements in paper staplers employing fixed surfaces for completing the staple formation include Watson U.S. Pat. No. 1,434,936. The latter discloses a multicomponent stapling head in which a staple forming block disposed above a mandrel is cammed to one side as a staple-driving plunger moves toward a fixed staple-forming surface.

Posnack U.S. Pat. No. 1,945,377 is directed to a stapling machine adapted to staple corrugated cardboard and employs a retractable anvil defining the stapler base which moves in the course of staple application. The Posnack stapler, if intended for use as a skin stapler, would be disposed in the center of the incision and slidably move thereover, thus rendering the same unfit for such use. Graf et al. U.S. Pat. No. 3,917,145 discloses a stapling machine having an arbor which pivots out of the staple former path following initial staple deformation. Such stapler is intended for use in limited space applications as in manufacturing of picture frames and could not be adapted for use as a skin stapler.

Other prior art directed to stapling devices particularly adapted for the stapling of paper and similar materials comprise Howensteine U.S. Pat. No. 456,415 and Swenson U.S. Pat. No. 1,610,632. The devices of these patents are adapted to form staples from a wire source, and although disclosing retractable elements in the course of staple formation, do not suggest a stapler construction of the type hereinafter described. Accordingly, these devices would be unsatisfactory for the purposes of the stapler of this invention, and would not suggest to a man skilled in the art the novel anvil retraction hereinafter described in detail or its attendant benefits.

Known skin staplers of the prior art include the surgical stapling instrument of the Becht et al. U.S. Pat. No. 4,179,057. This construction, however, does not disclose the novel retractable anvil of this invention nor the benefits resulting therefrom.

Savino U.S. Pat. No. 4,364,507 is directed to a variable closure surgical stapling apparatus with a retractable anvil. In Savino, however, the anvil must be retracted by a separate hand manipulation of the stapler user. Thus in the course of utilization of the Savino stapler a person utilizing the same must actuate both the driver blade to effect the desired staple deformation whereafter a second manipulation actuates a release blade for purposes of releasing the partially or completely deformed staple. Such stapler construction, accordingly, requires double finger manipulation including a driver blade manipulation in which the blade must be driven precisely to determine the desired degree of staple deformation, whereafter an anvil release blade is actuated. Such double actuation may be imprecise and undesired in emergency situations during which the immediate closing of a body opening is desired. Savino does not disclose or suggest the novel actuation of a retractable mandrel in the manner disclosed in the skin stapler hereinafter described in detail.

It is an object of this invention, therefore, to provide a novel skin stapler construction which is substantially jam-proof in the course of utilization, assuring the absence of stapler malfunction during emergency stapling situations wherein prompt closing of a body opening in a patient is of critical importance.

It is a further object of this invention to provide a skin stapler construction employing a novel retractable anvil construction in the course of staple deformation. The retractable anvil enables the stapler construction to be removed in any direction whatsoever from the site of staple application.

It is still a further object of this invention to provide a surgical stapler construction employing a sturdy and simple toggle arrangement which assures desired location of a staple-forming anvil during stapler operation. The provided stapler is of such design as to minimize the chances of mechanical malfunction during normal stapler use.

The above and other objects of this invention will become more apparent from the following detailed description when read in the light of the accompanying drawing and appended claims.

In one embodiment of the provided invention a surgical stapler construction is provided comprising a main stapler housing in which is disposed a staple guide rail. A reciprocally movable anvil member is disposed within the rail and has a distal end extending from the front stapler end. Staples are formed about the anvil distal end in the normal course of stapling operation.

The inner end of the anvil is connected to a toggle member, pivotally mounted within such housing. A stapler trigger member is movable into a central receiving opening in said housing and has spaced actuating surfaces for engaging and pivotally moving the toggle member both in the normal course of trigger actuation to clinch a staple, and in the course of trigger release.

In the normal stapling operation, the trigger actuates a former blade for purposes of forming an end staple disposed over the anvil distal end. Upon completion of the staple deformation or clinching, a trigger toggle-actuating surface engages a toggle arm to retract the anvil from the now-formed staple, allowing the stapler to be readily removed from engagement with the staple. The anvil is returned to its effective staple-forming position for use during a subsequent staple clinching step by a second actuating surface of the trigger member in the course of stapler trigger release as will hereinafter be described in greater detail. Thus, a novel anvil-toggle arrangement in the provided stapler assures desired location of the anvil relative to staples being formed thereon at the instant of desired staple deformation only, and assures retraction of such anvil from the vicinity of such staple immediately upon completion of the staple clinching. As a result there is no necessity for withdrawing the stapler in a particular direction relative to the formed staple, and jamming of a staple upon the distal end of the anvil is substantially eliminated.

Referring now more particularly to the drawing, it will be noted that:

FIG. 1 is a side elevational view of one embodiment of a surgical stapler made in accordance with this invention;

FIG. 2 is a top elevational view taken along line 2—2 of FIG. 1;

FIG. 3 is a front elevational view of the stapler embodiment of FIG. 1;

FIG. 4 is an end elevational view of the stapler embodiment of FIG. 1 taken along line 4—4 of FIG. 1;

Figure 5:
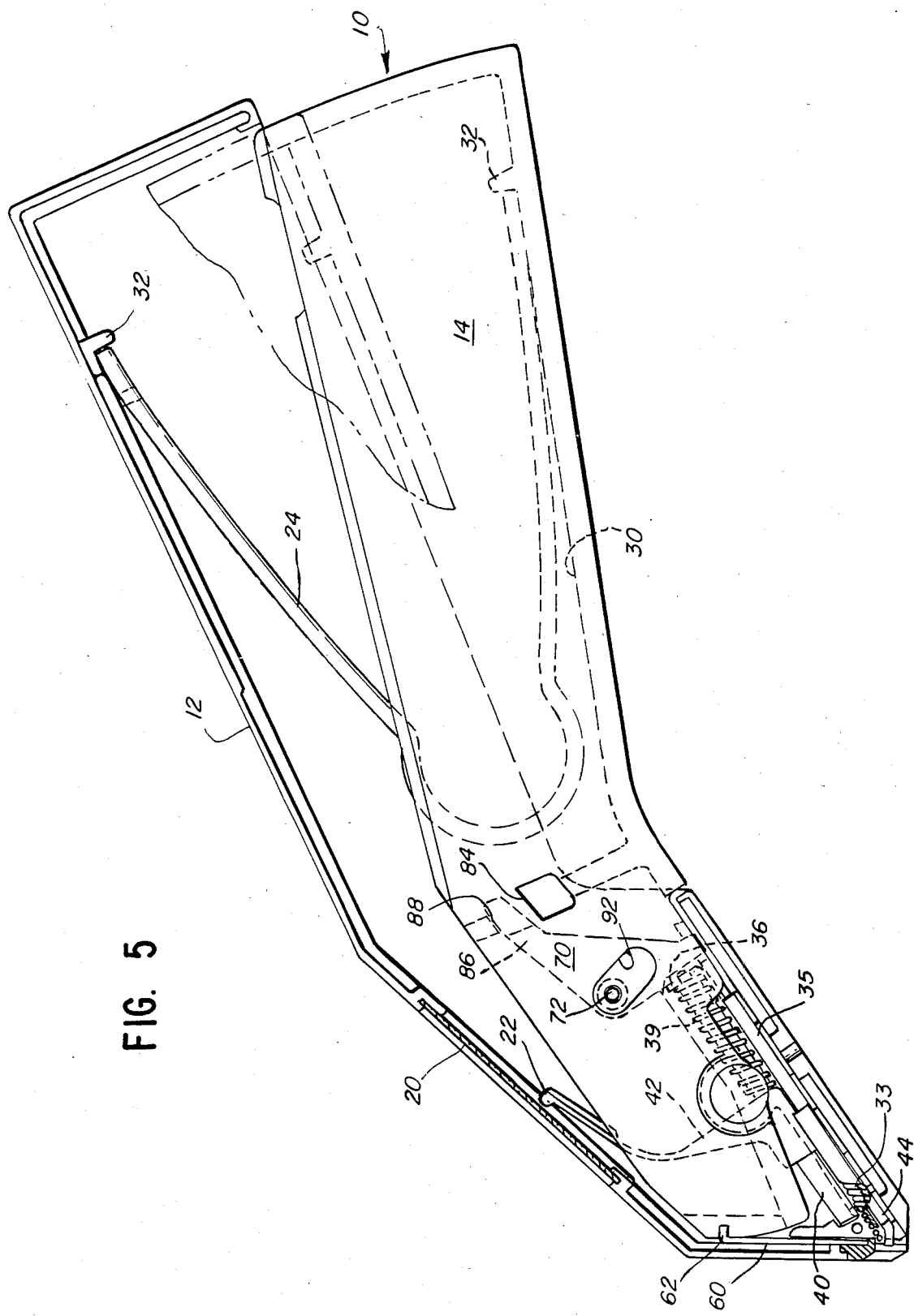
FIG. 5 is a side elevational view of one housing half of the stapler of FIG. 1, illustrating the manner whereby the centrally disposed trigger member is reciprocally movable relative thereto.

Referring more particularly to FIG. 1, a surgical stapler 10 made in accordance with the teaching of this invention is disclosed comprising a main housing member 12 into which a spring loaded trigger member 14 may be received following a squeezing, stapler-actuating operation effected by the user of a stapler. The stapler 10 is of a form and size so as to be readily and comfortably grasped by the hand of the stapler user. The stapler is employed by locating front flat nose portion 16 at the site of the body opening or wound to be closed, whereafter the trigger 14 is squeezed upwardly into the stapler housing body 14. As will be more apparent from FIG. 4 of the drawing, the trigger 14 is of lesser width so as to be received between the opposed wall portions of the larger stapler housing 12.

It will also be apparent from FIGS. 2 and 3 that disposed on an upper planar portion 18 of the stapler 10 is a window 20 having number gradations disposed along the length thereof, under which a stapler indicator 22 moves so as to readily visibly indicate to the stapler user the number of staples which remain for use. Trigger member 14 of the stapler 10 is resiliently biased outwardly relative to the housing 12 in which received by a spring member 24, see FIGS. 5 and 6.

Figure 6:
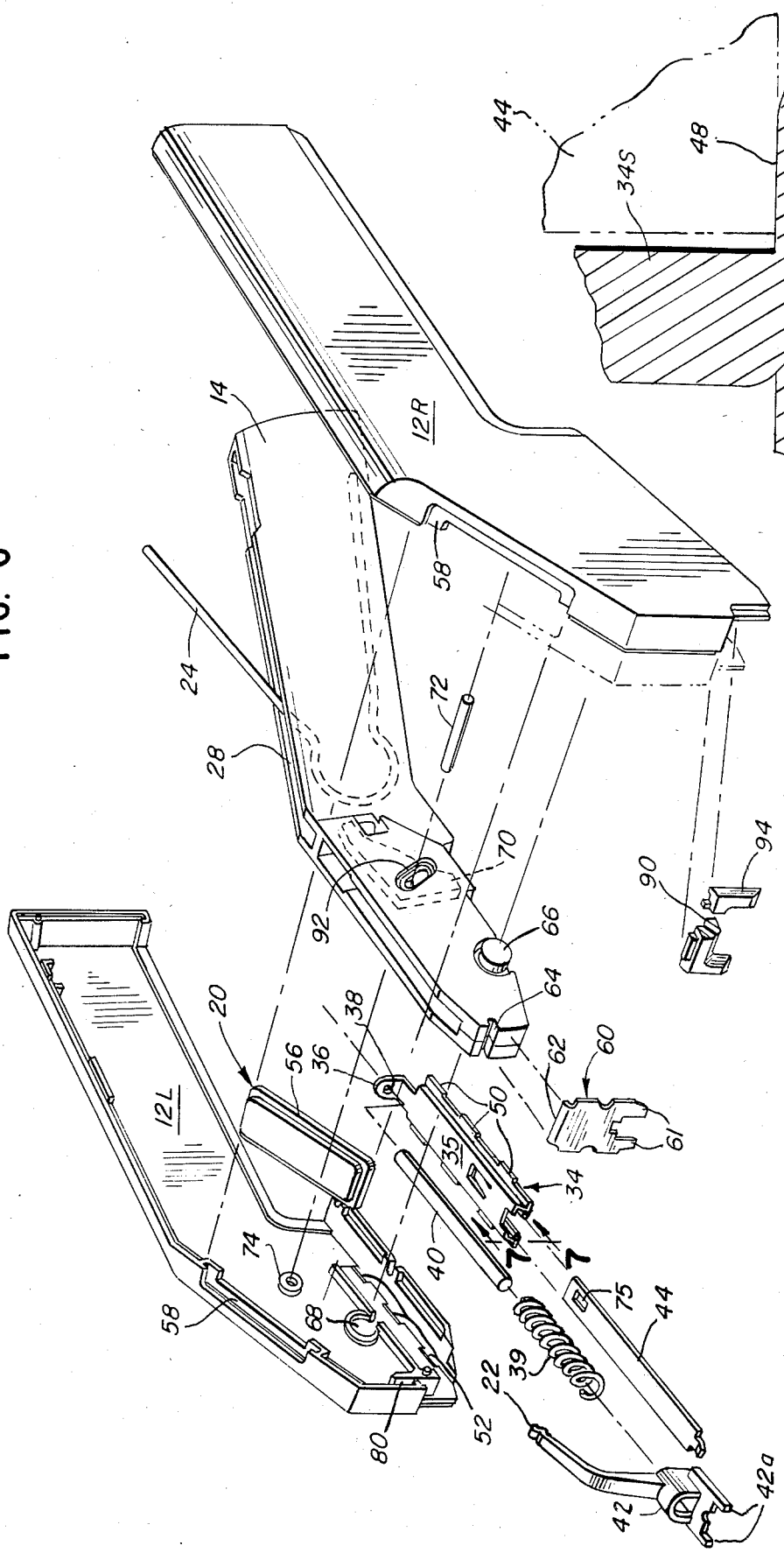
FIG. 6 is an exploded view illustrating the relationship between the various elements incorporated in the surgical stapler of this invention.

The various elements comprising the stapler 10 are illustrated in the exploded view of FIG. 6. It will be noted from FIG. 6 that the main stapler housing 12 comprises the opposed left and right housing portions 12L and 12R respectively which in the assembled position form the housing 12 of FIG. 1. FIG. 6 also indicates the general form of the trigger 14 having central slot 28 through which the upper arm of the spring 24 may extend for purposes of engaging a wall portion of the main housing 14 in the manner illustrated in FIG. 5. The lower arm of the biasing spring 24 engages floor 30 of the trigger 14 in the manner also illustrated in FIG. 5. Locating tabs 32 in the housing and trigger may serve to properly locate the ends of the spring 24 for desired trigger-biasing actuation.

Figure 8:
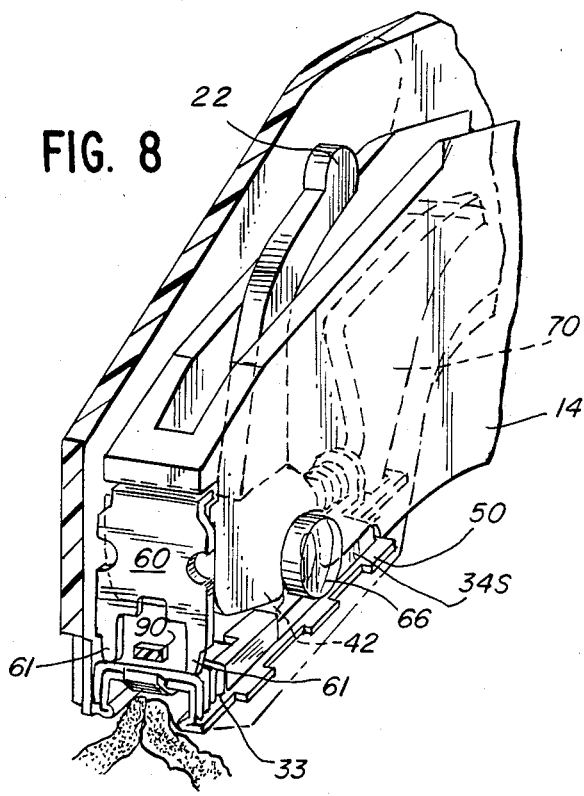
FIG. 8 is a fragmentary elevational view partly in section illustrating a stapler embodiment of this invention prior to forming a staple over the distal end of the stapler anvil member, the former blade being illustrated in engagement with the staple just prior to staple clinching.
Figure 9:
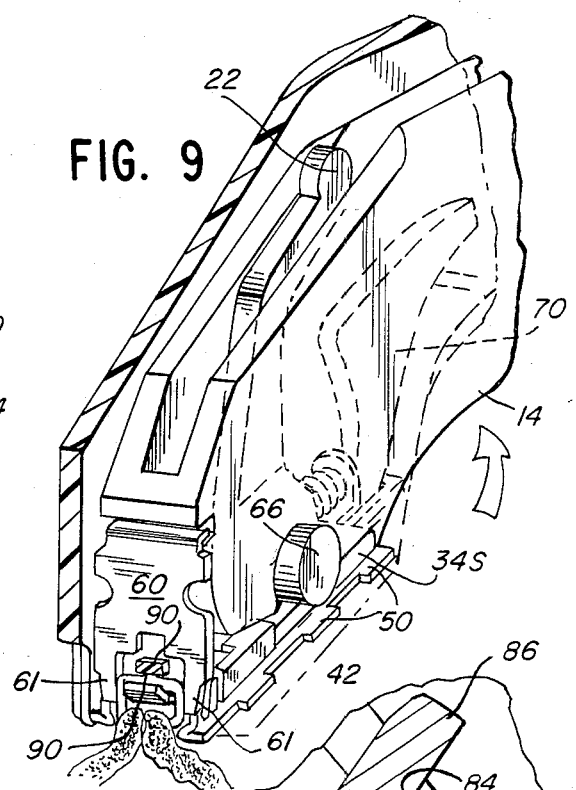
FIG. 9 is a figure similar to FIG. 8 but illustrating the former blade following staple clinching in the normal course of stapler use.

Staples 33 discharged at the nose portion 16 of the stapler 10, see FIG. 5, ride along a staple guide rail 34 as clearly seen in FIG. 6. It will be noted from the latter figure that the rail 34 is of substantially U-shaped crosssectional configuration enabling the staple bight portions to ride along rail planar upper surface 35 and the opposed staple legs to depend downwardly along opposed vertical sides 34S of the rail 34 (FIGS. 8, 9). The staple rail 34 has a vertical tab 36 disposed as its inner end portion and has an opening 38 therein for receiving and fixedly positioning one end of a spring guide post 40, see FIG. 6. One end of spring 39 abuts the vertical tab 36 and the opposite end of the spring abuts staple pusher 42 also illustrated in FIG. 6. Spring 39 is thus seen to be the biasing means which urges staples 33 toward the stapler end whereat the staples are discharged.

Figure 7:
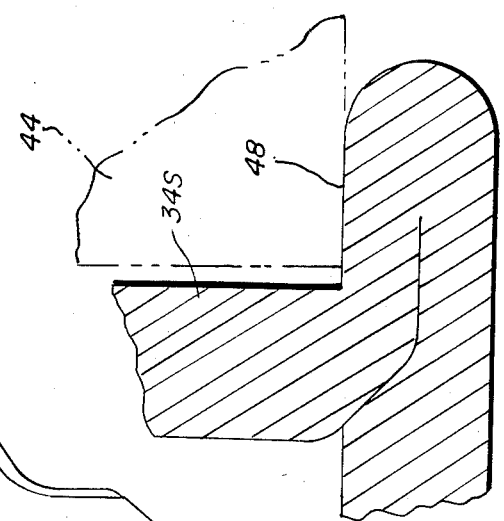
FIG. 7 is an enlarged fragmentary sectional view illustrating the manner whereby the staple rail incorporated in the stapler of this invention may be bent for purposes of forming a supporting track upon which the staple anvil of this invention may be reciprocally moved.

Received within the center recess of the rail 34 is an anvil member 44 as seen in FIG. 6. Opposed sides 34S, see FIG. 7, of the rail member 34 have the lower ends thereof bent through 180° radii as illustrated in FIG. 7, and have inwardly projecting ledge surfaces 48 extending from the opposed inner rail sides for purposes of supporting the reciprocally movable anvil member 44.

The opposed outer lateral edges of the staple rail 34 are formed as illustrated more clearly in FIG. 6 so as to define spaced, projecting tab portions 50 extending along the opposed side edges of the rail 34. The tabs 50 in the normal course of assembly are received in recesses 52 as illustrated in the housing portion 12L of FIG. 6. Similar recesses 52 are formed in opposed relationship therewith in the housing portion 12R illustrated in FIG. 6.

It will be noted from FIG. 6 that the staple pusher 42 not only has opposed staple pushing arms 42A but, in addition, has an upwardly extending arm terminating in indicator 22. The latter rides along the inner surface of window 20 as above described. The window 20 has peripheral edge portions 56 received in slot portions 58 disposed in the upper planar portion 18 defined by the opposed housing halves 12L and 12R.

It is the function of the trigger 14 to reciprocally move staple former blade 60 by virtue of engagement of former engaging tab 62 with receiving slot 64 disposed in front end portion of trigger 14 illustrated in FIG. 6. Trigger 14 is pivotally movable by means of pivot portion 66 formed on trigger 14 which is received in bearing portions 68 formed in housing portions 12L and 12R. Bearing portion 68 of housing half 12L is illustrated in FIG. 6. Illustrated in phantom lines in FIG. 6 is a pivotal toggle member 70 which in the normal course of assembly is pivotally mounted on pivot pin 72, the latter pin being mounted at opposed ends in bearings 74 formed integrally on opposed inner wall portions of the housing halves 12L and 12R. The toggle 70 is pivotally mounted on pin 72 in the normal course of assembly within the trigger slot 28 in the manner illustrated in FIG. 6.

Figure 10:
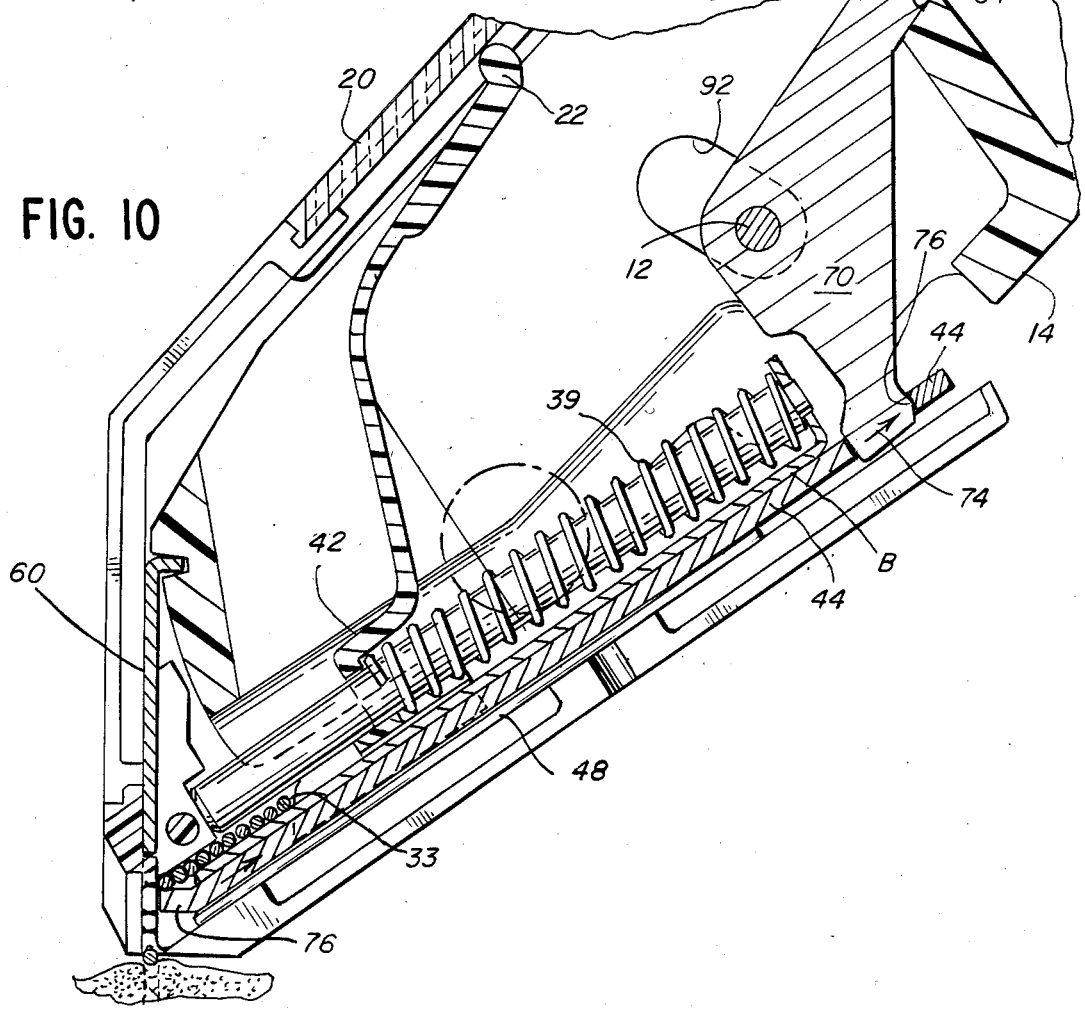
FIG. 10 is a fragmentary side elevational view partly in section, illustrating the relative position of the various stapler elements at the instant following staple clinching and retraction of the anvil incorporated on the stapler of this invention.

As is most apparent from FIG. 10 of the drawing, toggle 70 has an anvil-engaging foot portion 74 see FIG. 10, which is received within opening 75 formed in the inner end portion of anvil 44, (see FIG. 6). As is apparent from FIG. 10, pivotal movement of the toggle 70 about its pin 72 on which mounted results in reciprocal actuation of anvil 44 which is slidably housed within rail 34 as previously described.

The outer end 76 of anvil 44 is bent at an obtuse angle upwardly relative to the plane of the remainder of the anvil so as to effect a right-angle relationship with reciprocating staple former blade 60 in the manner clearly seen in FIG. 10. It will be noted from this figure that anvil 44 although freely reciprocally slidable within rail 34 is confined between bottom surface B of the rail planar surface 35 and the underlying rail supporting ledge surfaces 48 whereby the anvil reciprocal movement is substantially axial. Former blade 60 is guided in the course of its reciprocal actuation by the nose of the pivotally movable trigger 14 in appropriate slotted portions, such as portions 80 illustrated in the housing portion 12L in FIG. 6. In accordance with this invention, end anvil portion 76 disposed in substantially right angle relationship with the former blade 60 in the manner illustrated in FIG. 5, remains in such position until the end staple has been deformed thereover and clinched into, for instance, opposed edges of a wound to be closed as illustrated in FIG. 9.

FIG. 5 illustrates the stapler 10 in the condition of FIG. 1 ready for use for discharging a staple prior to squeezing of the trigger 14. FIG. 8 also illustrates the staple former 60 prior to effecting deformation of the end staple 33.

In the stapler position of FIG. 5, the trigger 14 is maintained in spaced relationship with the housing 12 by means of spring 24, and the former blade 60 is disposed with its opposed forming legs 61 adjacent the end staple 33. Upon squeezing of the trigger 14 into the center recess defined by the opposed housing half 12L and 12R, the trigger 14 pivots about pivot 66. Blade 60 will be driven downwardly, forming the end staple into crimped engagement with the edges of the body opening to be closed so as to arrive at the condition of FIG. 9.

In the normal stapler position, ready for use, illustrated in FIG. 5, the end portion 76 of the anvil 44 slidably retractable within the supporting rail 34, is disposed in underlying relationship with the former blade 60. As the trigger is squeezed upwardly into the position represented by the upper trigger outline in FIG. 5, into the body of the housing, the toggle 70 pivots about its pin 72. Simultaneously the anvil 44 is urged to rearwardly retract into the body of the stapler housing so that the anvil end portion 76 is retracted inwardly from the plane of movement of the former blade 60 as illustrated in FIG. 10. As a result, after a staple has been clinched into the skin-engaging position illustrated clearly in FIG. 9, the anvil 44 will be retracted from engagement with the deformed staple in the manner of FIG. 10 so as to allow the stapler construction to be readily removed from the site of the clinched staple without any danger of the anvil engaging the deformed staple to effect a pulling action on the clinched staple.

It is apparent from FIG. 8 that if the anvil 44 were allowed to remain in the position illustrated after the staple has been deformed into the condition of FIG. 9, the stapler would have to be retracted rearwardly or "backed off" from the formed staple so as to disengage the anvil from the staple. If the stapler were removed forwardly or upwardly after the staple clinching illustrated in FIG. 9, without anvil retraction, the stapler would tend to effect a tearing action as it would be pulling the clinched staple relative to the skin portions engaged.

It is thus seen that in accordance with the stapler construction of this invention the toggle action provided insures desired location of the staple-forming end 76 in the plane of the former blade 60 for purposes of effecting desired staple formation as in FIG. 8. In addition, the provided toggle arrangement assures retraction of the anvil end portion 76 from the plane of the reciprocally movable former blade so as not to comprise an obstacle to movement thereof.

The toggle 70 is actuated to pivot by structure illustrated in FIG. 10. As a result of engagement between ledge portion 84 of the trigger and projecting actuating arm 86 of the toggle, the toggle 70 is urged to pivot counter clockwise about pin 72 on which mounted. Following the desired stapling action illustrated in FIG. 9, the trigger 14 is released by the stapler user, thereby permitting the spring 24 to extend the stapler trigger 14 relative to the housing 12. In the course of trigger release, actuating ledge surface 88 formed in the stapler trigger, see FIG. 5, engages the toggle arm 86 to pivot the toggle 70 in a clockwise direction. Such engagement may function as a stop limiting the outward trigger movement relative to the housing 12. The outer staple-forming anvil end 76 is thereby returned into the initial position of use in the plane of the reciprocally movable former blade 60 in the manner illustrated in FIGS. 5 and 8.

It is thus seen that the opposed toggle-actuating surfaces 84 and 88 of the stapler trigger engage the toggle arm 86 for pivoting the same in counter clockwise and clockwise directions. Such engagements effect desired reciprocal movement of the anvil member 44, resulting in desired location of the staple forming end portion 76 of the anvil relative to the former blade 60.

To permit trigger movement relative to the stapler housing between the instants when the toggle arm 86 is engaged by the opposed actuating ledge surfaces 88 and 84 of the trigger member more clearly seen in FIG. 5 of the drawing, oval slots 92 are formed in the spaced walls of the trigger 4 in the manner clearly seen in FIG. 6 of the drawing. These slots 92 permit movement of the trigger relative to the housing without interference of movement from the toggle pivot pin 72.

Thus in accordance with this invention the staple anvil member 44 may be readily positioned into its desired staple-forming position by mere release of the trigger member. When it is desired to effect a desired stapling action, all that need be done is effect a simple trigger squeezing action. As a result thereof, a staple will be automatically clinched in the manner of FIG. 9. Simultanously the anvil member will be retracted inwardly by means of a toggle 70 into the retracted position of FIG. 10 so as not to interfere with any withdrawal of the stapler 10 from the deformed, clinched staple. The stapler 10 may be withdrawn in any direction relative to the deformed staples discharged therefrom without in any way comprising an obstacle to such withdrawal so as to effect pain or injury to the staple-receiving patient.

It may be desired for the attending surgeon to "air test" the stapler prior to actual utilization of the same in a surgical procedure, at which time he may merely wish to squeeze the trigger to determine whether a staple may be readily clinched in a desired manner without engagement of a receiving surface. During such air testing, the deformed staple which has been deformed on the anvil into the position of FIG. 9 may be stripped from engagement with the opposed former legs 61 by engagement with a stripper tab 90 projecting from inner surface of stapler closure member 94 (see FIG. 6). Closure 94 defines an opening in the stapler 10 from which the forming end 76 of the anvil projects. FIG. 9 of the drawing illustrates that when a staple is not retained by a skin of a receiving patient as during air testing, the staple will be readily stripped upon attempted retraction of the staple upwardly by the opposed legs 61 of the former 60.

Such staple stripping insures the absence of jamming as a result of a subsequent squeezing of the trigger with the first-deformed staple yet in engagement with the former blade. Accordingly, the provided stripper tab 90 assures the absence of jamming occasioned by a deformed staple being retained by the former 60 and effecting jamming in the course of a second stapler-deformation movement of such former.

The assembly of the various elements of the provided stapler construction is relately simple. The spring guide rod 40 is press fit into opening 38 of the vertical tab 36 of the staple rail. Anvil 44 is then slidably inserted into the rail interior. Staple pusher 42 is then mounted in opposition to spring 39 which is mounted on the guide rod 40. The guide rod is inserted through the receiving opening 41 of the pusher 42 and the toggle connected to the rail 34. The rail subassembly is then inserted into the receiving slot in the bottom of the trigger 14. Staple former 60 is then placed in the desired position relative to one housing half. The scale window 20 is placed in position, and the trigger spring is placed in desired position within the trigger in engagement of the opposed surface of one housing half with which assembled. The second housing half is then assembled with the trigger and secured to the first housing half by ultrasonic welding or other equivalent means of securing the two halves together. Following such assembly the staples may be loaded onto the staple rail after retracting staple pusher in opposition to the pusher spring 39. The front closure 94 may be then secured in place in the nose portion of the assembled stapler construction.

It is thus seen that the foregoing that a novel surgical stapler construction has been provided composed of elements which are substantially trouble-free. In the normal course of operation, the possibility of jamming is substantially eliminated. The provided stapler employs a novel anvil-retracting action which is automatically effected with the normal use of the stapler so as to assure desired retraction of the anvil end about which the end staple is bent and clinched. Following completion of the clinching, the stapler may be withdrawn in any direction whatsoever from the clinched staple. In the event the stapler is air tested, a deformed staple detained by blade 60 may be stripped from the legs 61 by means of the stripping tab 90 illustrated in FIG. 6 of the drawing.

Staplers of the foregoing type must be in a sterile condition at the time of use and distributed in sterile packaging. It is apparent that the stapler construction above described may be employed in reusable stapler constructions in which sterilization may take place repeatedly as by gas sterilization and the like. Accordingly, the stapler construction above described may be of a disposable type which is discarded once the staples have been utilized after a particular surgical procedure has been completed. As an alternative, the stapler may have a removable closure member for insertion of additional staples, with the staple pusher being readily retractable for purposes of inserting additional staples.

Although the above desoription relates to the closing of body openings occasioned by trauma or surgical incisions, the provided stapler may also be employed to advantage in various internal procedures within the body. Applied staples in such latter procedures may either remain within the body of the patient or be employed for a limited time period and removed prior to closing of the body surface opening.

It is apparent that modifications of the construction above described may be made without departing from the spirit of this invention. Accordingly, this invention is to be limited only by the scope of the appended claims.

What is claimed is:

1. A surgical stapler for clinching surgical staples in the body of a patient, comprising a housing; staple guide means in said housing for guiding surgical staples toward one end of said stapler; an anvil received within the guide means interior and having an end portion about which staples are formed; said end portion projecting from one end of said guide means; a reciprocally movable former in said housing for forming a staple about the anvil projecting end portion; a pivotally movable trigger movable relative to said housing for actuating said former into a staple-forming position relative to said anvil end portion; pivotal toggle means in said trigger connected to said anvil for translating pivotal movement of said trigger toward said housing into a slidable axial movement of said anvil away from said former after said former has deformed a staple about said anvil projecting end portion; said slidable axial movement being terminated as said trigger is moved toward said housing.

2. A surgical stapler for clinching surgical staples in the body of a patient, comprising a reciprocally movable anvil having a distal end portion about which a staple is formed; a reciprocally movable former movable in a plane intersecting with the anvil distal end portion when said end portion is at one end of its reciprocal movement for bendably forming a staple on said anvil end portion when said anvil end portion is at one end of its reciprocal movement; pivotally mounted toggle means connected to said anvil for moving said anvil in the course of its pivotal movement; and trigger means for simultaneously moving said former and said toggle means whereby said anvil end portion is withdrawn from the plane of said former substantially immediately after a staple is formed thereon by said former; said former being guided for reciprocal movement in guide portions of a stapler housing; the housing having a longitudinal slot within which said trigger means is movable and opposed side walls defining said slot between which said trigger means is pivotally mounted; pin means about which said toggle means is pivotally movable mounted on said housing opposed side walls; said trigger means having spaced walls between which said toggle means is pivotally mounted on said pin means; opposed slots disposed in said trigger means spaced walls for passage of said pin means and permitting pivotal movement of said trigger means relative to said pin means; said trigger means having spaced toggle-actuating means mounted between the trigger means spaced walls for pivotally actuating said toggle means in opposite directions of rotation about said pin means when said trigger means moves into and out of said stapler housing through said housing slot; biasing means engaging opposed surfaces of said trigger means and said stapler housing for outwardly biasing said trigger means relative to said housing; outward movement of said trigger means being limited by engagement of toggle-actuating means engaged by said toggle means as said trigger means moves outwardly out of said stapler housing.

3. A surgical stapler for clinching surgical staples in the body of a patient, comprising a reciprocally movable anvil having a distal end portion about which a staple is formed; a reciprocally movable former movable in a plane intersecting with the anvil distal end portion when said end portion is at one end of its reciprocal movement for bendably forming a staple on said anvil end portion when said anvil end portion is at one end of its reciprocal movement; pivotally mounted toggle means connected to said anvil for moving said anvil in the course of its pivotal movement; trigger means for simultaneously moving said former and said toggle means whereby said anvil end portion is withdrawn from the plane of said former substantially immediately after a staple is formed thereon by said former; said former being guided for reciprocal movement in guide portions of a stapler housing; the housing having a longitudinal slot within which said trigger means is movable and opposed side walls defining said slot between which said trigger means is pivotally mounted; pin means about which said toggle means is pivotally movable mounted on said housing opposed side walls; said trigger means having spaced walls between which said toggle means is pivotally mounted on said pin means; opposed slots disposed in said trigger means spaced walls for passage of said pin means and permitting pivotal movement of said trigger means relative to said pin means; said trigger means having spaced toggle-actuating means mounted between the trigger means spaced walls for pivotally actuating said toggle means in opposite directions of rotation about said pin means when said trigger means moves into and out of said stapler housing through said housing slot.

4. The surgical stapler of claim 3 or 2 in which said anvil is housed within a guide for staples fed into the plane of movement of said former; said anvil having an apertured inner end opposite to said distal end engaged by said toggle means in such manner that pivotal movement of said toggle means is translated into axial movement of said anvil within said guide.

5. The surgical stapler of claim 4 in which said guide for staples comprises a channel of substantially U-shaped sectional configuration including a substantially planar surface over which bight portions of staples may move in the course of being guided into the plane of movement of said former; said planar surface being connected to spaced substantially vertical side walls having terminal end portions bent inwardly beneath said planar surface and defining opposed anvil-supporting ledge surfaces whereby said anvil is supportably and reciprocally movable beneath said guide planar surface.

6. The surgical stapler of claim 5 in which the portion of said anvil connected to said anvil distal portion is so received between the bottom of said planar surface and said ledge surfaces whereby reciprocal movement of said anvil is substantially axial.

7. The stapler of claim 3 or 2 in which said former has a lip portion and said trigger means has an arcuate nose portion having a transverse slot for engagement with said former lip portion in such manner whereby pivotal movement of said trigger means reciprocally moves said former in a plane of movement within said stapler housing.

8. The surgical stapler of claims 3 or 2 in combination with guide means positioned in said housing for guiding surgical staples toward said former; means for pushing staples mounted on said guide means toward said former; transparent window means in said stapler housing over the pushing means; the pushing means having an indicator arm visible exteriorly of said stapler through said transparent window means for indicating the number of staples mounted on said guide means.

9. The surgical stapler of claim 3, 2 or 1 in which said former comprises a bifurcated blade having spaced staple-engaging legs separated by an intervening recess, and a staple stripping tab is located in the path of travel of said blade whereby such tab is traversed by said former in the course of moving toward said anvil and a staple retained by said former between the former legs is stripped from said former in the course of former movement away from said anvil.

* * * * *